(12) United States Patent
Fetz et al.

(10) Patent No.: US 6,457,973 B1
(45) Date of Patent: Oct. 1, 2002

(54) DENTAL IMPRESSION TRAY

(75) Inventors: Johann Fetz, Windach; Ingo Wagner, Steinebach; Joachim Zech, Kaufering, all of (DE)

(73) Assignee: ESPE Dental AG, Seefeld (DE)

( * ) Notice: Subject to any disclaimer, the term of this patent is extended or adjusted under 35 U.S.C. 154(b) by 0 days.

(21) Appl. No.: 09/714,517

(22) Filed: Nov. 17, 2000

(30) Foreign Application Priority Data

Nov. 22, 1999 (DE) .......................................... 199 56 103

(51) Int. Cl.[7] ................................................. A61C 9/00
(52) U.S. Cl. ........................................................ 433/37
(58) Field of Search ............................ 433/37, 38, 41, 433/42, 43, 44, 45, 46, 47, 48

(56) References Cited

U.S. PATENT DOCUMENTS

| | | | |
|---|---|---|---|
| 2,311,158 A | * | 2/1943 | Conway et al. ................ 433/36 |
| 4,085,507 A | * | 4/1978 | Lehn et al. ..................... 433/37 |
| 4,368,040 A | * | 1/1983 | Weissman ...................... 433/36 |
| 5,127,829 A | * | 7/1992 | Nordquist ...................... 433/37 |
| 5,190,457 A | * | 3/1993 | Schreinemakers ............. 433/37 |

FOREIGN PATENT DOCUMENTS

| | | |
|---|---|---|
| DE | 2619799 C2 | 5/1976 |
| DE | 19628682 A1 | 7/1996 |

* cited by examiner

*Primary Examiner*—John J. Wilson
(74) *Attorney, Agent, or Firm*—Connolly Bove Lodge & Hutz LLP

(57) ABSTRACT

A dental impression tray has a wall member which, in the working position of the tray, is disposed on the inner surface facing the jaw, is opposite the dental arch which faces the palate or tongue, respectively, and forms a flow surface for directing impression material into the region between a tooth or stub and the gingiva to prevent voids in the solidified impression.

8 Claims, 1 Drawing Sheet

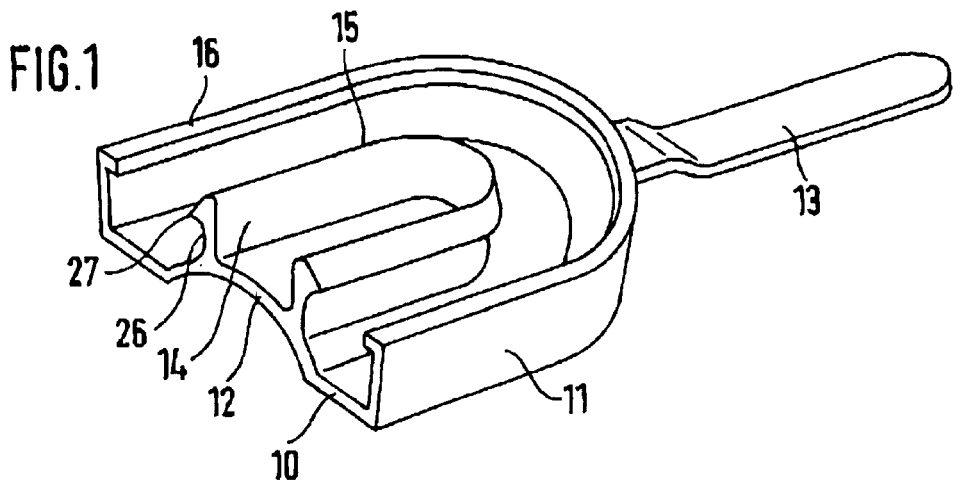
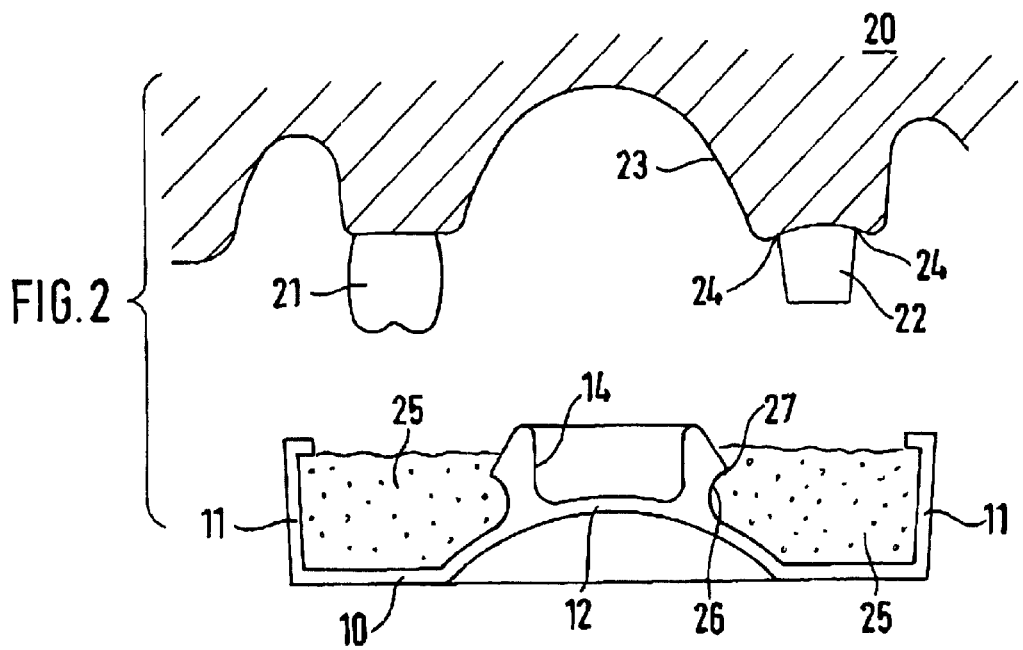
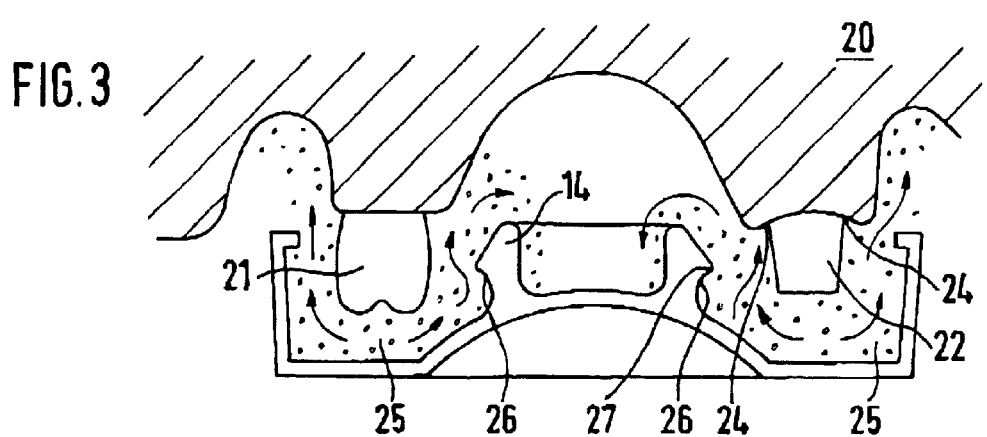

DENTAL IMPRESSION TRAY

BACKGROUND OF THE INVENTION

Dental impression trays are used for receiving a curable composition to obtain an impression of the dentition or part thereof. When plaster or another material is poured into said mould, a model of the dentition or part thereof can be obtained to serve as a working basis for the dental technician.

DE 26 19 799 C2, now issued in a related case as U.S. Pat. No. 4,085,507 to Lehn et al., discloses another dental impression tray which is similar to the one referred to above. It has inner and outer wall members provided with beaded terminal edges to exert a retentive force on the impression material.

DE 26 16 799 C2 discloses another dental impression tray which is largely similar to the one referred to above. It has inner and outer wall members provided with beaded terminal edges to exert a retentive force on the impression material.

Particularly with the use of silicones as the impression material, so-called flow streaks appear in the hardened material in the transitional area between tooth or stub and gingiva, i.e. voids which have not been filled out by the material flowing during the moulding process. Such voids are produced on account of the flow properties of the material when the tray filled with the impression material is fitted to the jaw, and these voids are additionally promoted by the hydrophobic property of the silicones. The material which is displaced by the teeth and the gingiva will flow in accordance with physical laws of flow past individual small undercuts intermediate the tooth and the gingiva, while the above-mentioned small voids may form similar to the burbling phenomenon on an airfoil.

These voids will corrupt the impression so that the subsequent work by the dental technician on such sites, which are important for fitting, will be made with insufficient precision thereby increasing the labour of the dental technician and/or the dentist, or in more severe cases the entire mould will become useless.

SUMMARY OF THE INVENTION

It is an object of the present invention to provide a dental impression tray with which precise impression may be taken. A more specific object of the invention may be seen in preventing the formation of the mentioned voids in the impression material.

To meet this object, the dental impression tray of the present invention has a wall member provided on an inner surface of the tray, the wall member, in the working position of the tray, facing the patient's jaw and being disposed at least partly opposite that side of the dental arch which faces the patient's palate or tongue, wherein the wall member has a surface with, at a terminal edge, extends towards a transition region between the patient's dental arch and gingiva.

When the tray is pressed against the jaw, this surface will cause the flow of the impression material to be directed into the transition area between the dental arch and the gingiva so that it cannot easily flow past narrow cavities or undercuts existing in said area but will rather fill out such formations. In this way the mentioned voids in the impression material can be eliminated or at least reduced, resulting in a better fit of the finished dental replacement part.

At the same time, the wall member results in a saving of moulding material.

In an embodiment, the surface of the wall member is concavely curved to permit the flow of the impression material to be directed in an even more controlled way to those sites which up to now could be filled only with difficulty.

Preferably, the terminal edge of the wall member, in the working position of the tray, cooperates with the patient's dental arch to form a region of reduced cross-section of flow. This leads to increased pressure in that portion where there is a tendency towards void formation.

The wall member may configured as a curved web which, in the working position of the tray, extends substantially along the entire dental arch so that the invention is effective throughout the dental arch.

Alternatively, the wall member is provided with the concavely curved surface along only part of its length, which makes the tray easier to manufacture.

In another preferred embodiment, the tray has an outer peripheral wall defining an outer top edge of the tray, and the wall member forms an inner top edge which is situated substantially above the outer top edge. In this configuration, the dental arch is prevented from being forced right through onto the bottom of the tray.

BRIEF DESCRIPTION OF THE DRAWING

FIG. 1 is a perspective view of a dental impression tray for the upper jaw,

FIG. 2 is a sectional view showing an upper jaw and the impression tray held in spaced relationship thereto, prior to taking an impression, and FIG. 3 is a view similar to FIG. 2 illustrating the situation when the dental arch is forced into the impression material.

DETAILED DESCRIPTION OF A PREFERRED EMBODIMENT

As shown in FIG. 1, the impression tray comprises a somewhat horseshoe-like base plate 10 having a peripheral wall 11 and an upwardly curved palatine plate 12 filling the central portion of the base plate 10. A handle 13 is attached to the proximal portion of the base plate 10.

A wall member 14 shaped like an arcuate web conforming to the horseshoe configuration of the base plate is formed integrally with the top of the palatine plate 12. The top edge 15 of the wall member is disposed substantially slightly above the top edge 16 of the peripheral wall 11.

The top portion of FIG. 2 is a schematic section through an upper jaw 20 including a tooth 21 and a stub 22. As is shown particularly at the stub 22, cavities, pockets and/or undercuts 24 are present in the transition area towards the gingiva 23.

The bottom portion of FIG. 2 is a section through the impression tray shown in FIG. 1 which has been filled with impression material 25 within the region confined by the base plate 10, the peripheral wall 11, a portion of the palatine plate 12 and the wall member 14.

As will be apparent from FIG. 2, the cross-section of the wall member 14 is designed so as to define a flow surface 26 which is concave towards the peripheral wall 11. The flow surface 26 terminates at an edge 27 and extends upwardly therealong at an angle of inclination which is about 45° in the illustrated embodiment.

When the tray is moved from the position illustrated in FIG. 2 towards the upper jaw 20, the upper teeth comprising the tooth 21 and the stub 22 will dig into the impression material 25 which is still soft. During this process the impression material 25 will be displaced and flow in the direction of the arrows indicated in FIG. 3.

In the working position of the tray illustrated in FIG. 3, the extension of the arcuate flow surface 26 points into the transition area between the stub 22 (or the tooth 21) and the surrounding gingiva and hence into the region where the cavities, pockets and/or undercuts 24 are present. Due to this configuration of the flow surface 26, the flow of the impression material 25 is directed by the wall member 14 into the transition area between tooth/stub 21/22 and gingiva 23 so that the impression material 25 is directed into the undercuts 24.

As will also be apparent from FIG. 3, the shape of the wall member 14 including the outwardly facing terminal edge 27 formed by the flow surface 26, on the one hand, and the opposing formation (tooth/stub 21/22), on the other hand, results in a region of reduced cross-section of flow. Thereby, the impression material 25 in this region is put under pressure and urged against the formation to be moulded, whereby filling-in of the undercuts 24 with the impression material 25 is promoted.

In the embodiment shown in FIG. 1 the wall member 14 extends across the entire arc of the impression tray. In order to facilitate the manufacture of the impression tray it may also be appropriate to configure the wall member 14 other than as a continuous arcuate web, i.e. to configure it so that the flow surface 26 will be effectively present only in the region of individual teeth or groups of teeth.

Also, the above embodiment is based on the assumption that the wall member 14 has a constant cross-sectional shape across the entire arc, especially as regards the configuration of the flow surface 26 and the terminal edge 27. However, it may also be suitable to vary the cross-sectional shape of the wall member 14 across the arc in order to still further improve the flow and pressure conditions of the impression material 25 in the individual portions of the jaw.

In addition to the function of preventing the formation of voids in the solidified impression material 25, the wall member 14 has the following desirable effects:

(1) The risk of the impression material 25 being penetrated right through, i.e. the risk of the dental arch being pressed onto the base plate 10 of the tray, is prevented by the feature that the wall member 14 due to its height will abut the patient's palate before the dental arch can make contact with the base plate 10. In this connection the flattened configuration of the wall member 14 above the terminal edge 27 of the flow surface 26 will form a support for the palate.

(2) The wall member 14 limits the flow of the impression material 25 into the palatine region so that a reduced amount of impression material 25 will be sufficient for a complete impression.

(3) The retching reflex, which is produced by the impression material 25 in the palatine region flowing down into the throat, is reduced. Such a retching reflex is not only inconvenient to the patient but also poses a problem in that it results in positional variations that prevent an undisturbed solidification of the impression material 25 while the impression tray is pressed against the jaw.

The embodiment illustrated in the drawing is directed to an impression tray for the upper jaw. The invention is likewise applicable to trays for the lower jaw even though the inner peripheral wall, which is frequently present in convention trays for the lower jaw and which serves the purpose of keeping the tongue region free, already results in flow conditions of the impression material where the risk of voids in the mould is reduced to some extent.

What is claimed is:

1. A dental impression tray for making an impression of a patient's jaw, comprising:

a wall member provided on an inner surface of the tray, said wall member being placed in a working position of the tray defined as a position facing the patient's jaw and being disposed at least partly opposite a side of a dental arch of the patient which faces a palate or a tongue of the patient, said wall member having a surface which, at a terminal edge, extends towards a transition region between the dental arch and a gingiva of the patient, said surface of said wall member being arranged above the inner surface of the tray to direct a flow of a dental impression material into the transition region;

wherein the surface of said wall member is concavely curved.

2. The tray of claim 1, wherein the terminal edge of said wall member, in the working position of the tray, cooperates with the patient's dental arch to form a region of reduced cross-section of flow.

3. The tray of claim 1, wherein said wall member is configured as a curved web which, in the working position of the tray, extends substantially along an entire extent of the dental arch of the patient.

4. A dental impression tray for making an impression of a patient's jaw, comprising:

a wall member provided on an inner surface of the tray, said wall member being placed in a working position of the tray defined as a position facing the patient's jaw and being disposed at least partly opposite a side of a dental arch of the patient which faces a palate or a tongue of the patient, said wall member having a surface which, at a terminal edge, extends towards a transition region between the dental arch and a gingiva of the patient, said surface of said wall member being arranged above the inner surface of the tray to direct a flow of a dental impression material into the transition region;

wherein said wall member has a concavely curved surface along only a portion of a length of said wall member.

5. A dental impression tray for making an impression of a patient's jaw, comprising:

a wall member provided on an inner surface of the tray, said wall member being placed in a working position of the tray defined as a position facing the patient's jaw and being disposed at least partly opposite a side of a dental arch of the patient which faces a palate or a tongue of the patient, said wall member having a surface which, at a terminal edge, extends towards a transition region between the dental arch and a gingiva of the patient, said surface of said wall member being arranged above the inner surface of the tray to direct a flow of a dental impression material into the transition region;

an outer peripheral wall defining an outer top edge of the tray, wherein said wall member forms an inner top edge, said inner top edge being situated above said outer top edge.

6. In a dental impression tray for making an impression of a patient's jaw, comprising:

a wall member provided on an inner surface of the tray, said wall member being placed in a working position of the tray defined as a position facing the patient's jaw and being disposed at least partly opposite a side of a dental arch of the patient which faces a palate or a tongue of the patient, said wall member having a surface which, at a terminal edge, extends towards a transition region between the dental arch and a gingiva of the patient, said surface of said wall member being arranged above the inner surface of the tray to direct a flow of a dental impression material into the transition region;

the method of taking an impression further comprising the steps:

providing impression material in the dental impression tray;

placing the dental impression tray adjacent to the patient's jaw; and forming an impression of the patient's jaw by moving the dental impression tray toward the patient's jaw, wherein the surface of the wall member interacts with the dental arch to urge impression material into a void in the transition region by reducing a flow cross-section and increasing a flow pressure of the impression material.

7. A dental impression tray for taking an impression of a patient's jaw, comprising:

a base plate;

a peripheral wall member extending above said base plate from an outer region thereof;

an inner wall member extending above said base plate from an inner region thereof, said peripheral wall member, said inner wall member, and a portion of said base plate defining a space for holding a dental impression material, said inner wall member having a surface opposite said peripheral wall member, said surface having a terminal edge remote from said base plate, a portion of said surface next to said terminal edge extending at an angle of inclination to cause the dental impression material to flow in an oblique outward direction away from said base plate;

wherein said surface of said wall member is concavely curved along at least a portion of a length of said wall member.

8. A method of taking a dental impression of a patient's jaw using a dental impression tray which includes a wall member provided on an inner surface of the tray and having a surface which, at a terminal edge, extends towards a transition region between a dental arch and a gingiva of the patient, the method comprising:

providing dental impression material in the dental impression tray;

placing the dental impression tray in a working position defined as a position facing the patient's jaw which is disposed at least partly opposite to a side of the dental arch which faces a palate or a tongue of the patient;

pressing the dental impression tray against the patient's jaw; and filling a void in the transition region, wherein the surface of the wall member at the terminal edge cooperates with the patient's dental arch to form a region having a reduced cross-section and an increased pressure of flow of the dental impression material into the transition region, wherein the reduced cross-section and the increased pressure of flow of the dental impression material allows the void in the transition region to be filled.

\* \* \* \* \*